(12) United States Patent
Laffay et al.

(10) Patent No.: US 10,420,648 B2
(45) Date of Patent: Sep. 24, 2019

(54) ACETABULAR PROSTHETIC SYSTEM WITH SIMPLIFIED IMPACTION

(76) Inventors: Jean-Pierre Laffay, Roppe (FR); Pascal Loehle, Belfort (FR); Frédérique Biegun, Bavilliers (FR)

( * ) Notice: Subject to any disclaimer, the term of this patent is extended or adjusted under 35 U.S.C. 154(b) by 59 days.

(21) Appl. No.: 12/456,034

(22) Filed: Jun. 10, 2009

(65) Prior Publication Data
US 2010/0318192 A1   Dec. 16, 2010

(51) Int. Cl.
*A61F 2/34* (2006.01)
*A61F 2/46* (2006.01)
*A61F 2/30* (2006.01)

(52) U.S. Cl.
CPC .............. *A61F 2/34* (2013.01); *A61F 2/4609* (2013.01); *A61F 2002/30822* (2013.01); *A61F 2002/3419* (2013.01)

(58) Field of Classification Search
CPC .............. A61F 2/34; A61F 2002/30332; A61F 2/4609; A61B 17/1666; A61B 17/92
USPC ............................................ 623/22.12, 23.12
See application file for complete search history.

(56) References Cited

U.S. PATENT DOCUMENTS

| | | | | |
|---|---|---|---|---|
| 3,829,904 A | * | 8/1974 | Ling | A61B 17/025 623/22.39 |
| 4,123,806 A | * | 11/1978 | Amstutz | A61F 2/32 623/22.39 |
| 4,262,369 A | * | 4/1981 | Roux | A61F 2/32 606/79 |
| 4,524,467 A | * | 6/1985 | DeCarlo, Jr. | A61F 2/32 623/19.12 |
| 5,571,200 A | * | 11/1996 | Cohen | A61F 2/34 623/22.12 |
| 6,022,357 A | * | 2/2000 | Reu | A61F 2/34 606/86 R |
| 6,027,505 A | * | 2/2000 | Peter | A61F 2/4637 606/91 |
| 6,129,765 A | * | 10/2000 | Lopez | A61F 2/468 623/22.15 |
| 6,132,469 A | * | 10/2000 | Schroeder | A61F 2/4637 606/99 |
| 6,468,281 B1 | * | 10/2002 | Badorf | A61F 2/4637 606/91 |
| 2003/0187512 A1 | * | 10/2003 | Frederick | A61F 2/32 623/22.2 |
| 2003/0216716 A1 | * | 11/2003 | Desarzens | A61B 17/1666 606/1 |
| 2004/0073226 A1 | * | 4/2004 | Cotting | A61F 2/34 606/91 |
| 2004/0186586 A1 | * | 9/2004 | Seyer | A61F 2/4609 623/22.12 |
| 2004/0225369 A1 | * | 11/2004 | Lakin et al. | 623/22.15 |
| 2005/0149047 A1 | * | 7/2005 | Parry | A61F 2/4609 606/99 |

(Continued)

*Primary Examiner* — Bruce E Snow
*Assistant Examiner* — Melissa A Hoban
(74) *Attorney, Agent, or Firm* — Renner Kenner Greive Bobak Taylor & Weber

(57) ABSTRACT

An acetabular prosthesis is adapted to be arranged in the acetabular of a patient for impacting it. The prosthesis includes a cup having a wall in the shape of a spherical cap intended to receive an insert within it. The outer surface of the cap is adapted to come into contact with the bottom of the patient's acetabular. The cap is extended at its peripheral edge by a cylindrical part, and at least one cavity is formed in the outer surface of the cylindrical part.

6 Claims, 4 Drawing Sheets

(56) References Cited

U.S. PATENT DOCUMENTS

| | | | |
|---|---|---|---|
| 2005/0261777 A1* | 11/2005 | Jones | A61F 2/30724 623/22.32 |
| 2006/0004463 A1* | 1/2006 | Lewis et al. | 623/22.38 |
| 2006/0167462 A1* | 7/2006 | Raugel | A61F 2/34 606/91 |
| 2006/0293686 A1* | 12/2006 | Wozencroft | A61F 2/4609 606/91 |
| 2007/0219562 A1* | 9/2007 | Slone | A61F 2/34 606/99 |
| 2007/0219640 A1* | 9/2007 | Steinberg | A61F 2/32 623/22.12 |
| 2008/0077249 A1* | 3/2008 | Gradel | A61F 2/4609 623/22.15 |
| 2010/0137870 A1* | 6/2010 | Shea | A61F 2/4637 606/91 |
| 2011/0060342 A1* | 3/2011 | Turner | A61F 2/4609 606/91 |

* cited by examiner

ACETABULAR PROSTHETIC SYSTEM WITH SIMPLIFIED IMPACTION

TECHNICAL FIELD

The present invention relates to an acetabular prosthetic system, to an ancillary system for gripping the acetabular prosthetic system, and to an assembly consisting of a prosthetic system and an associated ancillary system.

BACKGROUND ART

Acetabular prosthetic systems are well known in the field of orthopaedics. A prosthesis of this kind generally consists of a metal cup, or metal back, of substantially hemispherical shape, inside which is arranged an insert, for example made of polyethylene, in which is formed a cavity receiving a metal head. The whole assembly is intended to be received at the bottom of the patient's natural acetabulum.

To place the acetabular prosthesis at the bottom of the patient's acetabulum, and in particular to impact it at the bottom of the patient's acetabulum, there exist at present ancillary systems which screw into the bottom of the cup, the latter thus being pierced at its vertex. This is very detrimental with regard to wear once the cup is arranged in the acetabulum and therefore with regard to the life of this prosthesis. Another system consists in pressing on the inner wall of the cup. However, this solution does not work well, on account especially of a lack of adherence of the part of the gripping system which expands inside the cup to press against the inner wall of the cup at two diametrically opposed bearing points. This lack of adherence leads to untimely separation from the cup just when it is in fact desired to hold it for impaction.

DISCLOSURE OF THE INVENTION

The present invention aims to overcome the disadvantages of the prior art by providing an acetabular prosthesis which can be arranged, in particular impacted, very easily at the bottom of the patient's acetabulum without this involving piercing of the bottom of the cup, which adversely affects the life of the prosthesis. Furthermore, the prosthesis according to the invention can be held in a simple manner for reliable implanting of the cup.

According to the invention, the acetabular prosthesis, comprising a cup, having a wall in the shape of a spherical, in particular hemispherical, cap, a vertex and an opposite peripheral edge, and intended to receive within it an insert, in particular made of polyethylene, and its outer surface being intended to come into contact with the bottom of the patient's natural acetabulum, is characterised in that the spherical cap is extended at its peripheral edge by a cylindrical, in particular circular-cylindrical, part, and at least one cavity, preferably in the form of a peripheral groove, is formed in the outer surface of the cylindrical part.

By virtue of this cavity, which may for example be in the form of a groove which extends over the entire periphery, it is possible, with the aid of a gripper with a plurality of jaws, to engage on the outer surface of the cup close to its peripheral edge in order to insert it into the acetabulum and impact it therein.

According to a preferred embodiment of the invention, the at least one cavity consists of at least two cavities in the form of grooves, preferably of three cavities in the form of grooves, extending over a given angular distance and distributed uniformly along the outer peripheral edge of the cup. Thus, by using an ancillary in the form of a gripper with jaws which each engage in one of the grooves extending over a certain extension in the peripheral direction of the peripheral edge of the cup, very good attachment of the cup to the ancillary is obtained and therefore the prosthesis can be inserted into the acetabulum with great ease. At the same time, since the cavities are formed close to the peripheral edge of the prosthesis, no hole is formed in the part of the cup which comes into contact with the surface of the acetabulum of the person in which the cup is implanted, so that there is no risk of these cavities shortening the life of this prosthesis. In particular, the vertex part of the cup is not pierced, nor even the cup.

According to a preferred embodiment of the invention, the cup receives an insert, in particular made of polyethylene, of substantially hemispherical shape, which is articulated in this cup, in order thus to obtain what is called a dual-mobility prosthesis.

The present invention also relates to an ancillary for gripping an acetabular prosthesis for the purpose of arranging it in a patient's acetabulum, in particular impacting it therein.

According to the invention, the gripping system comprises a base body and at least two lugs, preferably three lugs, issuing from the base body, the lugs being in the shape of hooks, and there being provided means for permitting the parting of at least two hooks from one another in a reversible manner.

Thus, with the aid of this gripping system having hook-shaped lugs which can be parted for the purpose of positioning them in the cavities formed in the cup, there is obtained, after release of the parting, a clamping by the system for gripping the cup in order to introduce it and impact it in the acetabulum.

According to a preferred embodiment of the invention, the body of the gripping part consists of a U-shaped plate, a first lug being formed at the base of the U and the two other lugs being formed at the ends of the two limbs of the U, the U-shape permitting the parting of the two end lugs from one another to put in place the gripping system for gripping the cup.

According to a preferred embodiment of the invention, the lugs are shaped as a partial ring extending over a given angular distance, for example 30°.

BRIEF DESCRIPTION OF THE DRAWINGS

Embodiments of the invention given purely by way of example are now described with reference to the drawings, in which.

PREFERRED EMBODIMENT FOR CARRYING OUT THE INVENTION

Figure 1:
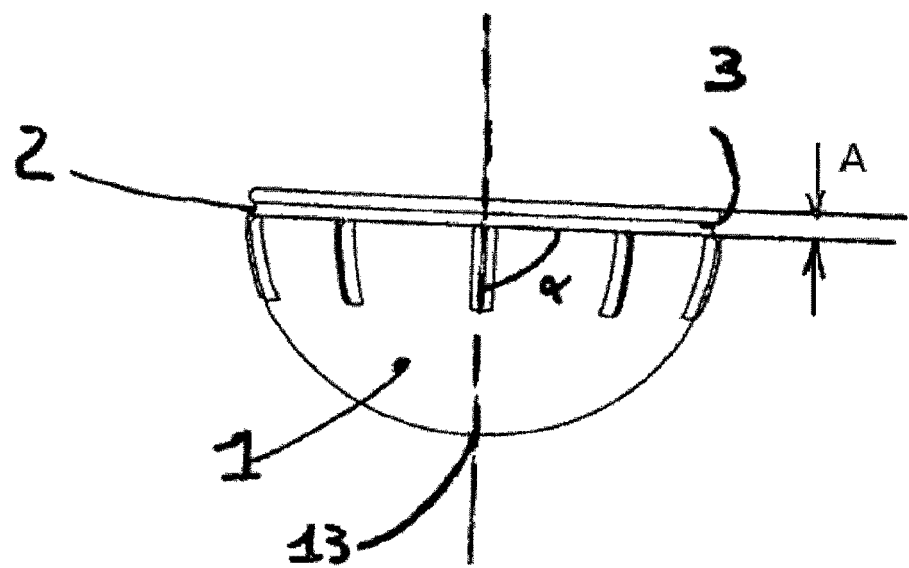
FIG. 1 shows an acetabular prosthesis seen from the side.

In FIG. 1, the outer part of a cup of an acetabular prosthesis according to the invention is shown. The cup comprises a hollow spherical cap 1 extending over an angle α of 90°, in cross-section at the centre. It would also be possible to provide a smaller or slightly larger angle of between 70° and 100°. The cup also comprises an end part 2 of circular-cylindrical or annular shape which extends the cap 1 over the entire periphery of the spherical cap 1. In this annular extension part 2 there is formed a peripherally extending groove 3. The annular part 2 extends between the peripheral edge 24 of the cap and the outer peripheral edge 25 of the cup. The thickness A of the annular part is preferably between 1 and 3 mm.

According to another embodiment (not shown), instead of a single groove 3, provision may be made for "partial" grooves spaced regularly along the annular part, for example three grooves in the form of slots.

Figure 2:
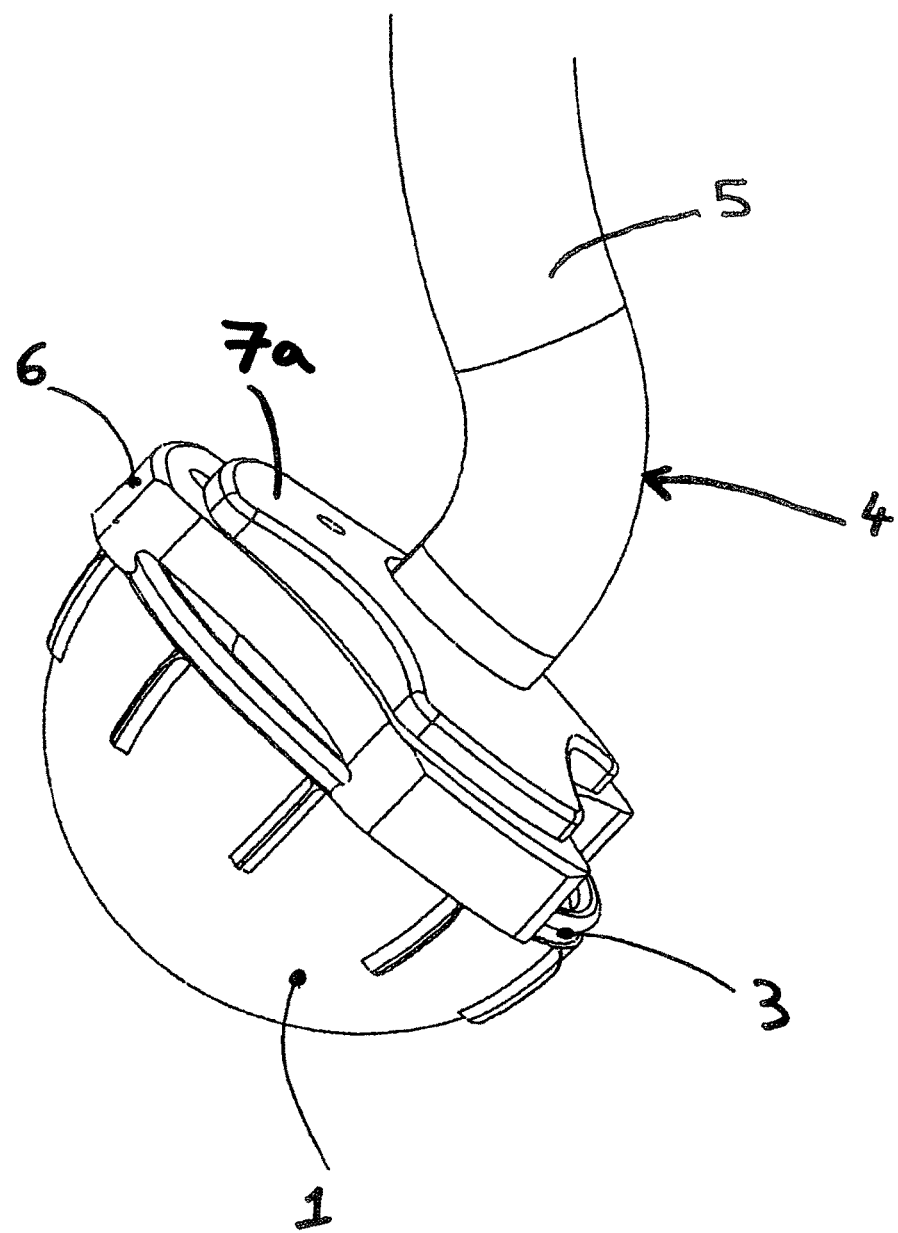
FIG. 2 shows the prosthesis of FIG. 1 and a gripping system according to the invention which is attached thereto for the purpose of implanting it in an acetabulum.
Figure 3:
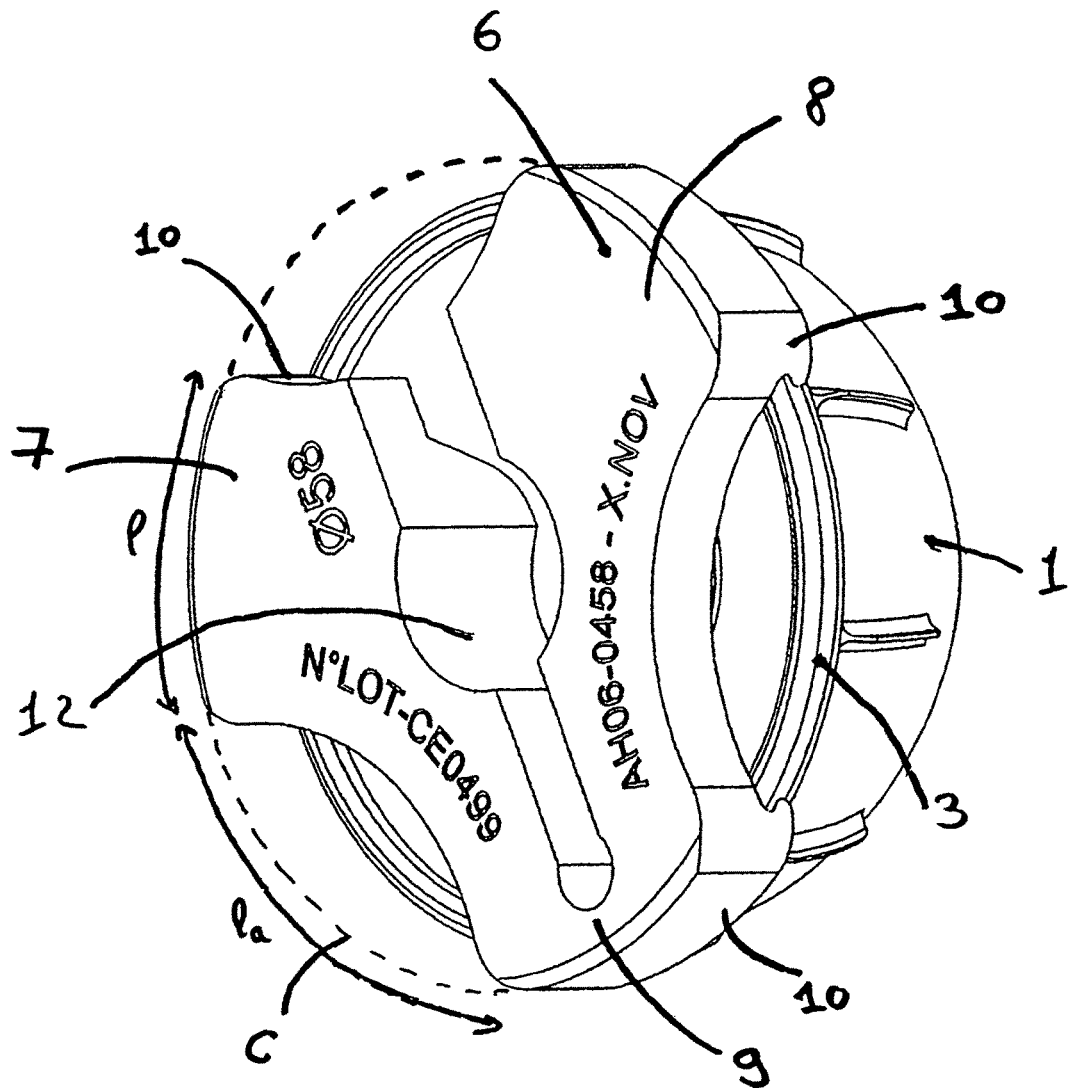
FIG. 3 is a plan view of the assembly of FIG. 2, but with the gripping rod omitted.

In FIG. 3, there can be clearly seen a part of the gripping system 4 shown in FIG. 2. The gripping system comprises a rod 5 connected to a plate 6 by a system 7a for fixing the rod to the plate. The plate 6 has a substantially U-shaped or V-shaped form, consisting of two limbs 7 and 8 which meet at a base 9. At each of the ends of the limbs 7 and 8, as well as at the base 9, there are formed lugs 10. These lugs 10 project from the plate in a direction perpendicular to the plane of the plate. These lugs 10 have in section, in a plane perpendicular to the plate, the shape of hooks, the attaching head of which is turned towards the inside of the plate. Along the imaginary circle C delimiting the plate, the lugs extend over a same partial arc length α. Along the circle C, the intervals $α_a$ separating the lugs are substantially equal.

The U-shaped form of the plate 6 as well as the low thickness of the base 9 of the U permit a deformation of the plate in order to part the limbs 7 and 8 from one another, then an elastic return of these two limbs towards one another. Thus, when it is desired to grip the cup 1, the lug 10 at the end of base 9 is positioned in the groove and the limbs 7 and 8 are parted to allow the two other ends to be inserted into the corresponding groove(s) 3. Thereafter, the two limbs 7 and 8 tend to return towards one another so as thus to clamp the cup between them. Particularly effective gripping of the cup by the plate lugs is thus obtained.

In particular, the lugs 10 do not protrude much beyond the outer surface of the cup and hardly extend over the outer surface of the cup, and especially not over the wall of the cap.

The rod is then introduced into the opening 12 and the cup can thus be introduced into the bottom of the acetabulum and impacted. Once the another again in order thus to withdraw the gripping system from the cup. As the jaw parts extend over a small distance laterally with respect to the base plane of the cup and extend little in the direction of the bottom of the cup, they do not come into contact with the wall of the acetabulum of the hip, and thus do not present any risk during the operation.

In particular, the groove or grooves 3 are situated substantially at the outer peripheral edge of the cup, in the annular extension part. The grooves or cavities are situated closer to the outer peripheral edge than to the vertex 13 of the cup.

Figure 4:
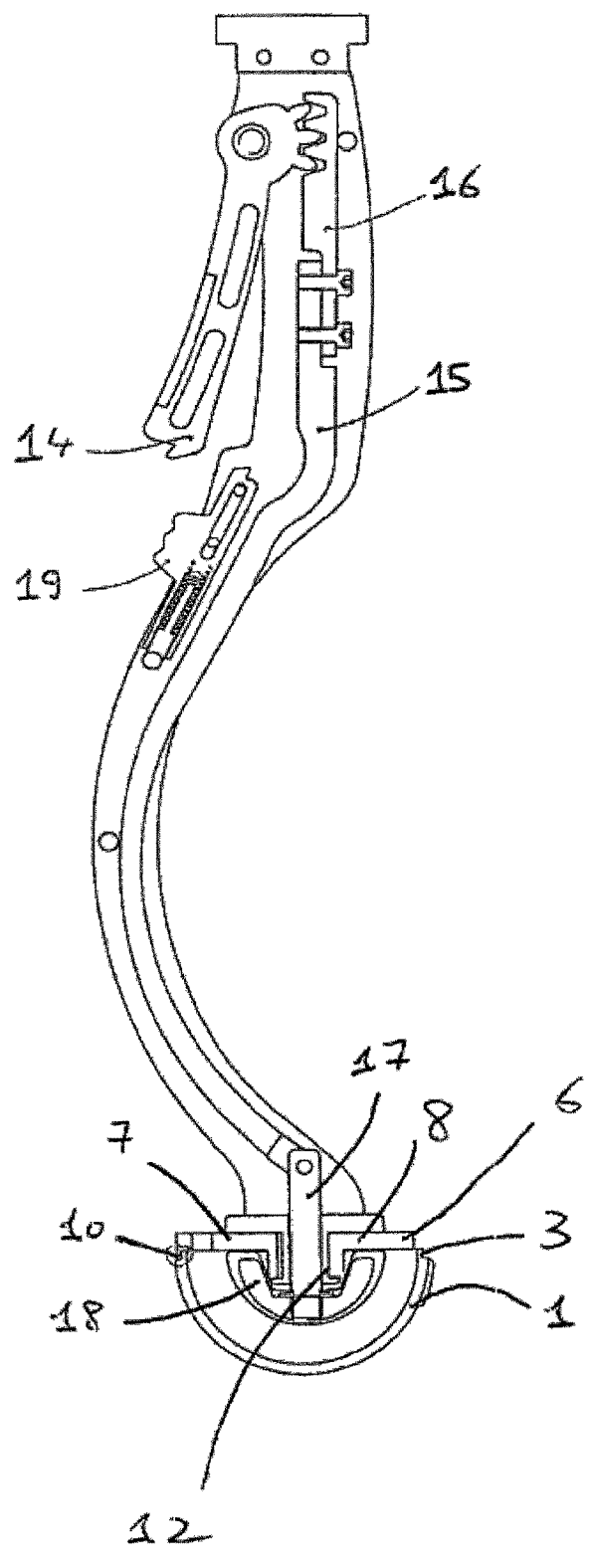
FIG. 4 shows a longitudinal sectional view of the prosthesis and the gripper attached thereto.

In FIG. 4, there can be seen in more detail the arrangement permitting the attachment and detachment of the cup to and from the gripping system, under the action of an actuating lever 14. This lever 14 cooperates with a toothed rack 16, which is itself attached to the force-applying rod 15, which is articulated at its other end to a pin 17. Situated at the opposite end of the pin 17 is a clamping cone 18. A lock 19 makes it possible to lock the assembly in the position shown in the figure in which the lever 14 is actuated downwards to attach the cup. When the lock is unlocked, the lever 14 can be actuated upwards to release the cup. The pin 17 passes through the hole 12 and the clamping cone 18 can press the two limbs 7 and 8 towards one another, as shown in FIG. 4, so that the lugs 10 penetrate into the grooves 3.

When it is desired to release the cup, the lock 19 is unlocked and the lever 14 is lifted, which has the effect of releasing the cone 18, the latter loosening its grip on the limbs 7 and 8, so that the latter move away from one another to free the lugs 10 from the grooves 3.

What is claimed is:

1. An assembly comprising an acetabular prosthesis for being arranged in the acetabulum of a patient and a gripping ancillary, said acetabular prosthesis including a cup having an inner surface for coming in contact with an insert and an outer surface for coming in contact with said acetabulum, said inner and outer surfaces being separated by an upper peripheral cup edge, said outer surface being at least in part of a spherical shape and extending from a bottom part to said upper peripheral cup edge, wherein said cup comprises a cap having an outer surface shaped in the form of a truncated sphere and an end part extending between said truncated sphere shaped cap and said upper peripheral cup edge, said sphere having a radius and a center, wherein said end part comprises a cavity in the form of a peripheral groove extending parallel to said upper peripheral cup edge continuously on 360 degrees around said cup and has an opening in said outer surface, said opening comprising an upper opening edge and a lower opening edge, wherein said upper opening edge is offset inwardly relative to said lower opening edge, wherein said lower opening edge, in an axial direction extending perpendicularly to a virtual plane delimited by said upper peripheral cup edge, is lower than said upper opening edge and said upper opening edge is lower than said upper peripheral cup edge, wherein said gripping ancillary includes at least one lug projecting through said opening between said upper opening edge and said lower opening edge and into said cavity for inserting said acetabular prosthesis, and wherein, in a vertical section, said outer surface of said cap is by a circular line portion included in a virtual circle having a radius corresponding to the radius of said sphere and a center corresponding to the center of said sphere, and said upper opening edge is offset inwardly relative to said virtual circle.

2. The assembly as defined in claim 1, wherein said at least one lug is in the shape of a hook.

3. The assembly as defined in claim 1, wherein the gripping ancillary includes a U-shaped plate, a first lug formed at the base of the U and second and third lugs formed at the ends of the two limbs of the U, the U-shape permitting the parting of the second and third lugs from one another to allow insertion of each lug in said cavity for gripping of the acetabular prosthesis.

4. The assembly as defined in claim 1, wherein said gripping ancillary comprises three lugs.

5. The assembly as defined in claim 1, wherein said gripping ancillary comprises at least two lugs and means for parting one of the at least two lugs away from another of the at least two lugs in a reversible manner so as to free the acetabular prosthesis from said gripping ancillary.

6. An assembly comprising an acetabular prosthesis for being arranged in the acetabulum of a patient and a gripping ancillary, said acetabular prosthesis including a cup having an inner surface for coming in contact with an insert and an outer surface for coming in contact with said acetabulum, said inner and outer surfaces being separated by an upper peripheral cup edge, said outer surface being at least in part of a spherical shape and extending from a bottom part to said upper peripheral cup edge, wherein said cup comprises a cap having an outer surface shaped in the form of a truncated sphere and an end part extending between said truncated sphere shaped cap and said upper peripheral cup edge, said sphere having a radius and a center, wherein said end part comprises a cavity is formed in having an opening in said outer surface, said opening being delimited by an upper opening edge and a lower opening edge, wherein said upper opening edge is offset inwardly relative to said lower opening edge, wherein said lower opening edge, in an axial direction extending perpendicularly to a virtual plane delimited by said upper peripheral cup edge, is lower than said upper opening edge and said upper opening edge is lower than said upper peripheral cup edge, wherein said gripping ancillary includes at least one lug projecting through said opening between, said upper opening edge and said lower opening edge and into said cavity for inserting said acetabular prosthesis, wherein said gripping ancillary comprises means for imparting to said at least one lug a movement which extends in a direction which is radial relative to said upper peripheral cup edge, and wherein, in a vertical section, said outer surface of said cap is delimited by a circular line, portion included in a virtual circle having a radius corresponding to the radius of said sphere and a center corresponding to the center of said sphere, and said upper opening edge being offset inwardly relative to said virtual circle.

* * * * *

UNITED STATES PATENT AND TRADEMARK OFFICE
CERTIFICATE OF CORRECTION

PATENT NO. : 10,420,648 B2
APPLICATION NO. : 12/456034
DATED : September 24, 2019
INVENTOR(S) : Jean-Pierre Laffay, Pascal Loehle and Frederique Biegun It is certified that error appears in the above-identified patent and that said Letters Patent is hereby corrected as shown below:

In the Claims

In Column 4, Line 37 (Claim 1, Line 29) the words "said cap is by" should read --said cap is delimited by--.

Signed and Sealed this
Twenty-sixth Day of November, 2019

Andrei Iancu
*Director of the United States Patent and Trademark Office*